United States Patent [19]

Jung et al.

[11] Patent Number: 4,709,115

[45] Date of Patent: Nov. 24, 1987

[54] DISPROPORTIONATION OF ALKENES

[75] Inventors: Chu W. Jung, Arlington, Mass.;
Philip E. Garrou, Charlotte, N.C.;
Gary R. Strickler, Midland, Mich.

[73] Assignee: The Dow Chemical Company, Midland, Mich.

[21] Appl. No.: 917,447

[22] Filed: Oct. 9, 1986

Related U.S. Application Data

[63] Continuation-in-part of Ser. No. 863,627, May 15, 1986, abandoned, which is a continuation of Ser. No. 473,928, Mar. 10, 1983, abandoned.

[51] Int. Cl.$^4$ .............................................. C07C 6/00
[52] U.S. Cl. ..................................... 585/643; 585/647
[58] Field of Search ................................. 585/643, 647

[56] References Cited

U.S. PATENT DOCUMENTS

| | | | |
|---|---|---|---|
| 3,448,163 | 6/1969 | Howman et al. | 585/647 |
| 3,676,520 | 7/1972 | Heckelsberg | 585/647 |
| 4,307,254 | 12/1981 | Smith | 568/697 |

Primary Examiner—Curtis R. Davis
Attorney, Agent, or Firm—M. F. Zuckerman

[57] ABSTRACT

A catalytic process for the disproportionation of alkenes in a distillation column reactor, whereby high conversion and selectivity are simultaneously achieved.

20 Claims, No Drawings

DISPROPORTIONATION OF ALKENES

CROSS-REFERENCE TO RELATED APPLICATION

This is a continuation-in-part of application Ser. No. 863,627, filed May 15, 1986, and now abandoned, which is a continuation of application Ser. No. 473,928, filed Mar. 10, 1983 and now abandoned.

BACKGROUND OF THE INVENTION

The present invention relates to the catalytic disproportionation of alkenes. Specifically, this invention relates to an improvement in the catalytic disproportionation of alkenes by use of a distillation column reactor.

According to this invention, the term disproportionation refers to the conversion of a hydrocarbon into similar hydrocarbons of both higher and lower numbers of carbon atoms per molecule. In the case of alkenes, a mixture of new products is obtained comprising alkenes of both higher and lower molecular weights. Such an operation is useful in many instances. For example, a more plentiful hydrocarbon can be converted to a less plentiful and, therefore, more valuable hydrocarbon. One instance of such a conversion occurs when the process of this invention is used to balance the alkene production of a naphtha cracking plant by disproportionating the large quantities of butenes into ethylene and hexene, or propylene and pentene. The disproportionation of butenes is a particularly valuable disproportionation reaction for the use of excess butenes. Approximately equimolar quantities of the higher and lower molecular weight alkenes may be produced by such disproportionation reactions. The higher molecular weight alkenes produced by disporportionation may be cracked to yield additional ethylene or propylene.

Much of the prior art describes conventional processes for the disproportionation of alkenes. Typically, the conventional process is carried out batchwise or in a continuous manner, using the catalyst in the form of a fixed bed, a fluidized bed or a moving bed. At the end of the reaction period, the hydrocarbon phase is separated from the solid catalyst phase and the hydrocarbon products are recovered. Well-known techniques, such as fractional distillation, solvent extraction and adsorption are employed for the separation of the hydrocarbon products.

Conventional processes for the disproportionation of alkenes, such as those described hereinabove, may be operated at temperatures as high as 500° C., but are unable to achieve simultaneous high conversion and high selectivity to desired products. See, e.g., Banks, R. L., J. Molecular Catalysis, V. 8, pp. 269–276 (1980). Alkene disproportionation reactions are reversible; therefore, theoretically the maximum conversion which can be achieved is limited by the thermodynamic equilibrium. In the disproportionation of butene-1 to ethylene and trans-hexene-3, for example, the conversion at equilibrium is about 50 percent. Selectivity is normally controlled by the catalyst and by process conditions, such as temperature, pressure and residence time. In a fixed bed reactor, the residence time is determined by the feed rate. In the disproportionation of butene-1, for example, a slow feed rate will result in a longer residence time for the propylene product, eventually leading to propylene disproportionation and the production of ethylene. On the other hand, a high feed rate will result in a short residence time for propylene and hence less ethylene in the product mix. Unfortunately, high feed rates reduce conversion; thus it is difficult to produce high conversion and high selectivity to propylene simultaneously. In addition, despite the numerous methods of controlling process conditions, many conventional disproportionation processes give broad product distributions, including the by-products of isomerization and secondary disproportionation reactions. Several illustrations of the prior art and its inherent limitations are presented hereinbelow.

U.S. Pat. No. 3,261,879 (1966) discloses a disproportionation of olefin hydrocarbons by contact with a catalyst containing molybdenum oxide or tungsten oxide in a conventional reactor. Conversions are taught to vary over a wide range; however, at high conversion a broad distribution of $C_{2-12}$ olefinic products is shown. Isomerization yields are taught to be high.

U.S. Pat. No. 3,463,827 (1969) discloses a process for the disproportionation of olefins by contact with a Group VIB metal carbonyl associated with alumina, silica or silica-alumina. The process is conducted in a fixed bed reactor, and the products are separated in a fractionation column. Conversions are taught to be low, less than 20 percent for butene-1, and isomerization tends to be high.

U.S. Pat. No. 3,448,163 (1969) describes a conventional process for the disproportionation of olefins employing a catalyst comprising rhenium heptoxide impregnated on alumina. In the disproportionation of butene-1, the combined selectivity to ethylene and hexenes is taught to be 93 percent at a conversion of only 29 percent.

U.S. Pat. No. 3,641,189 (1972) discloses a conventional olefin disproportionation process utilizing a rhenium heptoxide catalyst supported on alumina. High selectivities are accompanied by low conversion of the feedstock. U.S. Pat. No. 3,642,931 (1972) teaches a conventional olefin disproportionation process employing a catalyst comprising rhenium heptoxide supported on a refractory oxide of zirconium, thorium, tin, or mixtures thereof. The degree of disproportionation is taught to be less than 15 percent.

U.S. Pat. No. 3,676,520 (1972) discloses a method of disproportionating olefins by contacting the olefin with a catalyst comprising rhenium oxide and a support, such as alumina. The process is carried out in any of the aforementioned standard reactors. In the disproportionation of propylene, the conversion is taught to be less than 5 percent at high contact temperature. There are no teachings on how to control the selectivities of higher olefins, such as butenes.

In view of the deficiencies of the prior art methods, it would be desirable to possess a process for the disproportionation of alkenes which would be capable of achieving simultaneous high conversion and high selectivity at moderate temperatures. It would also be desirable to possess a process for the disproportionation of butenes, such that a high yield of ethylene or propylene, and the corresponding hexenes or pentenes, could be achieved by a simple adjustment of the operating conditions. Such a process would easily meet the demands for varying olefin feedstocks. It would also be desirable to obtain the disproportionation and the separation of products simultaneously, since any reduction in the number of process steps offers considerable economic advantages.

SUMMARY OF THE INVENTION

The present invention is such a process for the disproportionation of alkenes, involving contacting at least one alkene with a catalyst in a distillation column reactor under such reaction fractionation conditions that there is formed at least one product of the disproportionation of at least one of the alkenes. By use of the distillation column reactor, this disproportionation and the separation of products are advantageously conducted simultaneously. Surprisingly, the process of the present invention proceeds with high selectivity at high conversion at moderate temperatures. More surprisingly, the process of the present invention, as applied to butenes, can be controlled to give high yields of ethylene or propylene, whichever is desired, and the corresponding hexenes and pentenes by simple adjustments in the operating conditions. By all of the aforementioned accomplishments, the present invention satisfies a long-felt need for improvement in the art of disproportionating alkenes.

DETAILED DESCRIPTION OF THE INVENTION

Alkenes which are subject to disproportionation according to the process of the present invention include acyclic alkenes having at least 3 carbon atoms, and their aryl derivatives and mixtures thereof. Preferred are alkenes having from 3 to about 30 carbon atoms and mixtures thereof. More preferred are mono-1- and 2-alkenes, such as, for example, butene-1, and mixtures of these alkenes, such as, for example, a mixture of butene-1 and butene-2. Most preferably, the process of the present invention is applied to butene-1 or a mixture of butene-1 and butene-2. Optionally, an inert material may be included in the alkene fed to the distillation column reactor. Examples of said inert materials include nitrogen, the inert gases of Group VIIIA, such as helium and argon, and alkanes, such as methane, propane and butane.

Catalysts suitable for use in the process of the present invention are those materials which catalyze the disproportionation reaction when used in the process of the present invention, and include conventional catalysts used for the disproportionation of alkenes. Examples of said conventional catalysts include supported materials which contain catalytic metals such as rhenium, molybdenum or tungsten, and which optionally include a promoter, such as tetramethyltin or tetrabutyltin. Preferred catalysts comprise rhenium or a rhenium compound or complex having an alumina support. Rhenium oxides are preferred for use in the catalysts of the process of the present invention. The support materials can be in a variety of forms, and may contain other materials which do not substantially promote undesirable side reactions. Preferably, any conventional catalytic grade of alumina or silica-alumina may be used as the support. Gamma-alumina is the most preferred support material.

The composite catalyst is prepared by suitable methods such as dry mixing, impregnation or coprecipitation. Catalytic metal oxides or compounds convertible to catalytic metal oxides by calcination are suitably employed in the catalyst preparation. A convenient method for the preparation of the catalyst is to dry blend the catalytic metal oxide, such as rhenium oxide, and the support in a ball mill where intimate contact between the finely divided particles is achieved. The milled composite can be pressed into pellets or tablets of various sizes and shapes. Additionally, the finished catalyst may be in the form of granules as well as in other shapes, such as agglomerates, spheres, extrudates and the like, or it may be employed in such conventional distillation packing shapes as Raschig rings, saddles and the like. If desired, pelleted catalysts can be crushed to obtain particles having specific mesh size.

After the catalytic metal oxide, or compound which may be converted to a catalytic metal oxide by calcination, is associated with the support, the composite is subjected to a calcination or activation step before being utilized in the olefin conversion process. The activation technique comprises heating at elevated temperatures in the presence of a suitable flowing gas. Air is a preferred activation gas, although other gases, for example, inert gases such as nitrogen or the noble gases, may be used, provided that at least part of the catalytic metal present in the catalyst composition is in the oxide form at the completion of the activation. In some instances, the catalyst may be heated serially in more than one gas. The catalysts are subjected to a temperature which is generally in the range of 300° C.-700° C. for about 0.5 to 20 hours or longer. Generally, longer activation periods are used with lower temperatures, and shorter activation periods are used with higher temperatures. Either way, the selectivities to the disproportionation products are the same.

The activated catalyst may be used, without regeneration, for runs of up to several days or more, and may be regenerated. The regeneration is accomplished by suitable methods for regenerating oxide catalysts and may comprise the same steps used in the activation procedure.

The distillation column reactor employed in the present invention is suitably a distillation column having therein a catalyst for the disproportionation of alkenes. Any type of distillation tower may be employed in the process of the present invention, provided that a fixed bed of catalyst may be created therein to fill the reaction-distillation zone or portions thereof. The catalyst packing is of such a nature as to allow vapor flow through the catalyst, while also providing sufficient surface area to catalyze the disproportionation reaction.

The distillation column reactor is operated so as to disproportionate the alkenes in the feed stream and separate the products therefrom simultaneously. Accordingly, the reactor may be operated under any conditions, e.g., temperature and pressure, at which disproportionation is achieved. Thus, the temperature within the column will be related to the boiling point of the alkene starting material, and to the pressure in the column. Typically, the operating temperature in the distillation column reactor may range from about −50° C. to about 300° C., and preferably will be from about 0° C. to about 150° C. The pressure in the distillation column reactor typically will be from about zero to about 1000 psig and preferably will be from about 50 to about 300 psig. Higher or lower temperatures and pressures may be employed; however, beyond the lower end of the range the reaction will proceed slowly, if at all, and beyond the higher end of the range, undesirable side reactions and coke formation may occur. Additionally, it will probably be more expensive to operate outside the ranges given.

The process of the present invention is a method for the simultaneous disproportionation of alkenes and distillation of the product mixture as it forms. For example, when butene-1 is fed to the distillation column reactor, it contacts the catalyst and is selectively disproportionated to ethylene and 3-hexene. The ethylene immediately upon formation ascends through the distillation column reactor, and the 3-hexene descends in accordance with conventional principles of distillation. Consequently, the reverse reaction, whereby 3-hexene and ethylene combine to form 1-butene, does not occur. Thus, in contrast to prior art disproportionation methods, which were capable of achieving high conversion with low selectivity or high selectivity at low conversion, the process of the present invention surprisingly is capable of obtaining simultaneous high conversion and high selectivity.

For the purposes of this invention, the term conversion refers to the elimination of the alkenes in the feed stream from the reaction mixture. For example, in the practice of this invention, butene-1 may be converted substantially to ethylene and hexene-3 under the proper conditions using a distillation column reactor wherein butene-1 is held in the central portion of the column and isnot allowed to escape. For the purposes of the present invention, the term selectivity refers to the percentage of the converted feed which goes to the desired major products.

The concept of simultaneous high selectivity and high conversion may be expressed conveniently in terms of yield. For the purposes of the present invention, the term "yield" refers to the numerical product of conversion and selectivity. For example, a process according to the present invention operating at a conversion of 0.75 and a selectivity of 0.90 would have a yield of 0.675, which is the numerical product of 0.75 and 0.90. The process of the present invention may be operated to give higher yields that prior art disproportionation processes. Typical yields of the process of the present invention are at least about 65 percent, based upon moles of alkene in at least about 75 percent. Most preferably, the yield will be at least about 85 percent.

A great deal of control over the rate of reaction and the distribution of products can be achieved simply by adjusting the operating conditions of the reaction system. For example, the temperature in the system may be increased by increasing the pressure and the feed rate may be adjusted to control the percent conversion. The process of the present invention is additionally advantageous in that a great degree feed which goes to the desired major products. the process of the present invention are at least about 65 percent, based upon moles of alkene in the feed stream. Preferably, the yield will be at least about 75 percent. Most preferably, the yield will be at least about 85 percent. conditions of the reaction system. For example, the temperature in the system may be increased by increasing the pressure, and the feed rate may be adjusted to control the percent conversion. The process of the present invention is additionally advantageous in that a great degree of control may be exercised over the percentage of propylene and ethylene produced simply by adjusting the residence time of the process. It is known that the residence time may be altered by changing any of a number of process variables, such as the feed rate, the length or height of the distillation column reactor, and the overhead temperature. When a low overhead temperature is maintained, propylene remains in contact with the catalyst for a longer time, eventually disproportionating to ethylene and butene-2. Alternatively, when a high overhead temperature is maintained, propylene leaves the column faster. Thus, for any fixed column length, the selectivity to ethylene or propylene can be controlled to a large extent by simply controlling the overhead temperature. In either case, the conversion is high in the distillation column reactor; thus, high yields of ethylene or propylene can be produced, as desired, to meet the varying olefin feedstock requirements.

The number of theoretical trays, the fractionation conditions, including temperature and pressure, the reflux and reboil control system, the number and location of side streams, the flow rate, etc., are those which are used in conventional engineering practice and can be determined by conventional design calculations and procedures. The fractionating apparatus employed in the process of the present invention may be operated using known process control techniques.

When an alkene or a mixture of alkenes is fed to a distillation column reactor under conditions previously described herein, the alkene or alkenes will be disproportionated to products having boiling points lower and higher than the boiling point of the alkene feed stream. Further, the process proceeds with high conversion and simultaneous high selectivity.

Specific Embodiments

The following examples and catalyst preparations are given to illustrate the invention and should not be construed as limiting its scope. All percentages in the examples are mole percent unless otherwise indicated. Two comparative examples are given to illustrate the reaction in a conventional fixed bed reactor.

Preparation of Catalyst A

A mass (25 g) of gamma-alumina in the form of $\frac{1}{8}'' \times \frac{1}{8}''$ tablets is added to a solution prepared by dissolving 3.35 g of $Re_2O_7$ in 250 ml of aqueous ethanol (5–10 percent $H_2O$). The resulting mixture is stirred under vacuum for a few minutes and is then evaporated to dryness on a steam bath. The resulting light grey pellets are dried at 100° C. for 3 hours and are then calcined in a dry air stream at 600° C. for 1 hour. Plasma emission analysis, using the 346.05 nm rhenium line, indicates a 9.04 percent rhenium loading.

Preparation of Catalyst B

A catalyst is prepared according to the method of preparation of Catalyst A except that sufficient $NH_4ReO_4$ is added to the aqueous ethanol to give a 2 percent rhenium loading. Analysis of the resulting catalyst indicates a 1.55 percent rhenium loading.

Preparation of Catalyst C

A catalyst is prepared according to the method of preparation of Catalyst A except that the catalyst is subjected to an additional calcination treatment at 500° C. in a stream of water-saturated air (0.2 SCFH) for 2 hours. The catalyst has a 9.2 percent rhenium loading, as determined by plasma emission analysis.

Preparation of Catalyst D

A catalyst is prepared according to the method of preparation of Catalyst A except that sufficient $NH_4ReO_4$ is added to the aqueous ethanol to give a 2.5 percent rhenium loading. The catalyst is subjected to a calcination treatment at 600° C. for 3 hours in a muffle furnace open to the air. This treatment allows the catalyst to collect moisture from the air upon cooling. The catalyst has a 2.0 percent rhenium loading, as determined by plasma emission analysis.

EXAMPLE 1

A distillation column reaction vessel is constructed from 316 stainless steel pipe. The main body of the vessel has a ¾-inch outside diameter and the remainder of the vessel has a ⅜-inch outside diameter. The main body of the vessel is filled to a depth of approximately ½ inch with glass Raschig rings. Catalyst A (25 g) is added to the main body of the vessel to form a catalyst bed having an approximate size of 9 inches by ⅜ inch. The remaining space in the main body of the vessel above the catalyst is filled with ⅛ inch diameter 304 stainless steel beads. The void volume of the reactor including reboiler is 70 ml, measured with the catalyst and inert packing in place. A thermosiphon reboiler is attached below the main body of the vessel. The vessel is equipped with a condensing means, means for controlling the temperature in the reboiler, means for heating the main body of the vessel, means for observing and recording the temperature at various points in the vessel, means for observing and controlling the pressure, and means for emergency relief of an overpressure condition.

Butene-1 is fed at a rate of 9.0 g per hour (60 ml/min, measured at Standard Temperature and Pressure, STP) into the reboiler of the vessel. The temperature in the reboiler is maintained at 115° C., the temperature in the overhead condenser is maintained at −50° C., and the pressure in the system is maintained autogenously at approximately 80 psig. The butene-1 flashes from the reboiler into the catalyst bed where the bulk of the butene reacts at a temperature of less than 100° C. The higher boiling hexene-3 product fractionates immediately from the butene. The lower boiling ethylene product separates from the butene, passes through the condenser, and is removed from the system. The average flow rate of vapor from the top of the vessel is 30 cc/min., measured at STP.

The overhead stream is analyzed using vapor phase chromatography and is found to be 90 mole percent ethylene and 10 mole percent propylene. The bottoms stream is analyzed using vapor phase chromatography and is found to be approximately 69.7 mole percent hexene-3, approximately 11.0 mole percent pentene, approximately 14.7 mole percent butene-1, approximately 3.7 mole percent heptene, and approximately 0.9 mole percent octene. The overall conversion is 92 mole percent, calculated according to the formula:

$$\% \text{ conversion} = \frac{\text{moles of butene-1 converted}}{\text{moles of butene-1 fed}} \times 100.$$

The selectivity to the various products and by-products, based on the moles of butene-1 converted, is as follows:

| Species | Mole % Selectivity |
| --- | --- |
| Ethylene | 45.1 |
| Propylene | 4.9 |
| Pentenes | 6.5 |
| Hexenes | 41.3 |
| Heptenes | 2.2 |
| Octenes | 0.5 | wherein $$\% \text{ selectivity} = \frac{\text{moles of species formed}}{\text{moles of butene-1 converted}} \times 100.$$

Absolute mole values, rather than relative mole ratios, are used in making these calculations, because the overhead stream and the bottoms stream contain, different total moles of products. Thus, the yield of ethylene and hexene is approximately 79.5 percent, calcuated as follows:

| | | |
| --- | --- | --- |
| selectivity to (C$_2$ + C$_6$) | = 0.451 + 0.413 | = 0.864 |
| conversion | = 0.92 | |
| yield | = 0.92 × 0.864 | = 0.795. |

EXAMPLE 2

The method of Example 1 is repeated with the following exceptions:
(a) Catalyst B is employed (24 g);
(b) the feed rate of 1-butene is 9.6 g/hour;
(c) the reboiler temperature is 130° C.; and
(d) the system pressure is maintained autogeneously at 90 psig.

Analyses of the product streams and the selectivities, calculated as in Example 1, are shown in Table I.

TABLE I

| | Overhead (mole %) | Bottoms (mole %) | Selectivity (mole %) |
| --- | --- | --- | --- |
| Ethylene | 98 | — | 49 |
| Propylene | 2 | — | 1 |
| Butenes | — | 31 | — |
| Pentenes | — | 1 | 0.7 |
| Hexenes | — | 68 | 49.3 |
| Heptenes | — | — | — |
| Octenes | — | — | — |

The overall conversion is 85 mole percent and the combined yield of C$_2$+C$_6$ hydrocarbons is about 84 percent.

EXAMPLE 3

The method of Example 1 is repeated, with the following exceptions:
(a) Catalyst C is employed (30 g);
(b) the feed rate of 1-butene is 9.6 g/hour;
(c) the reboiler temperature is 120° C.;
(d) the overhead temperature is approximately 28° C; and
(e) the system pressure is maintained autogeneously at 100 psig.

Analysis of the product streams and the selectivities, calculated as in Example 1, are shown in Table II.

TABLE II

| | Overhead (mole %) | Bottoms (mole %) | Selectivity (mole %) |
| --- | --- | --- | --- |
| Ethylene | 26 | — | 17 |
| Propylene | 49 | — | 32 |
| Butenes | 24 | 40 | — |
| Pentenes | 1 | 12 | 11 |
| Hexenes | — | 41 | 36 |
| Heptenes | — | 6 | 4 |
| Octenes | — | <1 | <1 |

The overall conversion is 68 mole percent. Higher conversions may be readily attained by maintaining the overhead temperature below 0° C. to constrain the 1-butene to the reactive zone. This example demonstrates the disproportionation of butene-1 into desired $C_2$, $C_3$, $C_5$ and $C_6$ products in a yield of approximately 65 percent. Thus, as can be seen by comparing the results of Examples 1 and 3, the product mix may be varied by changing, in a simple manner, the catalyst preparation and the process operating conditions, most notably the overhead temperature.

EXAMPLE 4

The method of Example 1 is repeated, with the following exceptions:
(a) Catalyst D is employed (23 g);
(b) the feed rate of 1-butene is 9.6 g/hour;
(c) the reboiler temperature is 130° C.;
(d) the overhead temperature is 0° C.; and
(e) the system pressure is maintained autogeneously at 90 psig.

Analyses of the product streams and the selectivities, calculated as in Example 1, are shown in Table III.

TABLE III

|  | Overhead (mole %) | Bottoms (mole %) | Selectivity (mole %) |
|---|---|---|---|
| Ethylene | 2 | — | 1 |
| Propylene | 96 | — | 49 |
| Butenes | 2 | 14 | — |
| Pentenes | — | 35 | 20 |
| Hexenes | — | 47 | 27 |
| Heptenes | — | 3.5 | 2 |
| Octenes | — | 0.5 | 0.3 |

The overall conversion is 92 mole percent. The combined yield of $C_3$ and $C_5$ hydrocarbons is about 64 percent, while the combined yield of $C_2$, $C_3$, $C_5$ and $C_6$ hydrocarbons is about 89 percent. Thus, as can be seen by comparing the results of Examples 2 and 4, the product mix may be varied by changing the catalyst preparation in a simple manner and by changing the overhead temperature.

Comparative Experiment 1

A catalyst comprising gamma-alumina in the form of $\frac{1}{8}'' \times \frac{1}{8}''$ tablets and $Re_2O_7$ is prepared following the procedure described in the preparation of Catalyst A except the catalyst is calcined overnight in dry air at 530° C. Plasma emission analysis, using the 346.05 nm rhenium line indicates an 8.38 percent rhenium loading. The catalyst (25 g) is added to a vessel to form a fixed bed reactor having an approximate size of 9 inches by $\frac{3}{8}$ inch. Butene-1 is fed at a rate of 50, 150 or 200 ml/min into the reactor. The temperature of the bed is maintained at 50° C. or 100° C. The pressure is maintained at 1 atmosphere in order to keep the butene in the gaseous state. The product stream is analyzed using vapor phase chromatography, and the product distribution is given in Table IV.

TABLE IV

| C.E. 1 | Flow ml/min | Temp °C. | Conv. mole % | Selectivity (mole %) |  |  |  |
|---|---|---|---|---|---|---|---|
|  |  |  |  | $C_2H_4$ | $C_3H_6$ | $C_5H_{10}$ | $C_6H_{12}$ |
| (a) | 50 | 100 | 44.8 | 35.0 | 32.6 | 18.0 | 14.4 |
| (b) | 150 | 50 | 40.5 | 40.4 | 5.2 | 4.0 | 50.4 |
| (c) | 200 | 50 | 34.8 | 39.1 | 3.8 | 3.6 | 53.5 |
| (d) | 200 | 100 | 40.8 | 36.5 | 19.9 | 15.3 | 28.3 |

Comparison of Example 1 with Comparative Experiment 1(a), shows that the conversion in the fixed bed reactor is less than one-half the conversion in the distillation column reactor. Furthermore, the combined yield of ethylene and hexene, calculated as in Example 1, is only 22.1 percent in the fixed bed reactor, or less than one-third of the analogous yield in the distillation column reactor. At higher flow rates illustrated by Comparative Experiments 1(b), (c) and (d), the conversion in the fixed bed reactor decreases. Thus, in contrast to Example 1, a high conversion and high selectivity cannot be obtained simultaneously in the fixed bed reactor. Accordingly, a high yield of $C_2 + C_6$ hydrocarbons cannot be achieved under mild conditions.

EXAMPLE 5

The method of Example 1 is repeated, with the following exceptions:
(a) the feed is an equimolar mixture of butene-1 and butene-2, with the butene-2 being 50 percent cis and 50 percent trans;
(b) the feed rate is 20 g/hour;
(c) the reboiler temperature is 130° C.;
(d) the overheads temperature is approximately 5° C.;
(e) the system pressure is maintained autogeneously at 100 psig; and
(f) the average vapor flow rate from the top of the vessel is 120 cc/min.

Analyses of the product streams and selectivities, calculated as in Example 1, are shown in Table V.

TABLE V

|  | Overhead (mole %) | Bottoms (moles %) | Selectivity (mole %) |
|---|---|---|---|
| Ethylene | 7 | — | 3 |
| Propylene | 92 | — | 47 |
| Butenes | 1 | 23 | — |
| Pentenes | — | 49 | 30.7 |
| Hexenes | — | 27 | 19.3 |
| Heptenes | — | — | — |
| Other | — | <1 | — |

The overall conversion is 88 mole percent and the yield to propylene and pentenes is approximately 68.4 percent. The combined yield of $C_2$, $C_3$, $C_5$ and $C_6$ hydrocarbons is 88 mole percent. Thus, it is seen that by making simple adjustments in the feedstock and the operating conditions of Example 1, the selectivity can be controlled to provide a high combined yield of $C_3$ and $C_5$ hydrocarbons.

Comparative Experiment 2

A rhenium catalyst (8.38 percent Re) is prepared according to the procedure of Example 1, except that the catalyst is calcined at 530° C. overnight in air. The fixed bed reactor of Comparative Experiment 1 is employed with 25 g of the rhenium catalyst. An equimolar mixture of butene-1 and butene-2, with butene-2 being 50 percent cis and 50 percent trans, is fed to the reactor at a rate of 20 g/hour. The temperature of the bed is maintained at 50° C., 75° C. or 100° C. The pressure is maintained at 1 atmosphere so as to keep the butenes in the gaseous state. The product stream is analyzed using vapor phase chromatography and the product distribution is given in Table VI.

TABLE VI

| C.E. 2 | Temp °C. | Conv. mole % | Selectivity (mole %) |  |  |  |
|---|---|---|---|---|---|---|
|  |  |  | $C_2H_4$ | $C_3H_6$ | $C_5H_{10}$ | $C_6H_{12}$ |
| (a) | 50 | 48.6 | 36.6 | 7.67 | 3.71 | 34.5 |
| (b) | 75 | 40.3 | 36.5 | 20.6 | 11.7 | 34.5 |
| (c) | 100 | 61.7 | 5.11 | 44.4 | 34.8 | 13.5 |

Comparison of Example 5 with Comparative Experiment 2(b), shows that the conversion in the fixed bed reactor is less than 50 percent of the conversion in the distillation column reactor. Furthermore, the combined yield of $C_3$ and $C_5$ hydrocarbons in the fixed bed reactor is only 13 percent, compared with 68 percent in the distillation column reactor. Even at 100° C., the combined yield of $C_3$ and $C_5$ hydrocarbons in the fixed bed reactor is only 49 percent, as shown in Comparative Experiment 2(c).

It may be noted that the conversions shown in Examples 1–5 are for a column fed at the reboiler. Conversions will be higher for a properly designed and operated distillation column reactor having the feed point located at a point in the column such that the feed alkene(s) may be retained in the catalyst bed until said alkene(s) are disproportionated.

As previously mentioned, the preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A process for the disproportionation of alkenes, comprising contacting a composition containing at least one alkene with a catalyst containing at least one rhenium compound or complex in a distillation column reactor er such reaction and fractionation conditions that there are formed products of the disproportionation of at least one of said alkenes, and such that the combined yield of said products is at least about 65 mole percent.

2. A process according to claim 1 wherein the catalyst contains a mixture of alumina and at least one rhenium compound or complex.

3. A process according to claim 2 wherein the alumina is gamma-alumina.

4. A process according to claim 1 wherein a composition containing butene-1 is contacted with a catalyst in a distillation column reactor under such reaction and fractionation conditions that ethylene and hexene are formed.

5. A process according to claim 1 wherein a composition containing butene-1 is contacted with a catalyst in a distillation column reactor under such reaction and fractionation conditions that ethylene, propylene, pentene and hexene are formed.

6. A process according to claim 5 wherein the yield of ethylene, propylene, pentenes and hexenes is at least about 85 mole percent.

7. A process according to claim 1 wherein a composition containing butene-1 and butene-2 is contacted with a catalyst in a distillation column reactor under such reaction and fractionation conditions that propylene and pentene are formed.

8. The process of claim 4 wherein ethylene and hexene make up at least about 75 mole percent of the higher and lower molecular weight alkenes formed by the process.

9. The process of claim 7 wherein the yield of ethylene, propylene, penetenes and hexene is at least about 85 mole percent.

10. A high yield process comprising contacting butene-1 and a catalyst, which comprises rhenium heptoxide and alumina, in a distillation column reactor under such reaction and fractionation conditions that ethylene and hexene are produced.

11. A process comprising contacting butene-1 and butene-2 and a catalyst, which comprises rhenium heptoxide and alumina, in a distillation column reactor under such reactor and fractionation conditions that propylene and pentene are produced.

12. A process for the disproportionation of alkenes comprising contacting a composition containing at least one alkene with a catalyst containing at least one rhenium compound or complex in a distillation column reactor, wherein the opening temperature of the distillation column reactor is in the range from about −50° C. to about 300° C., and the pressure is in the range from about 0 psig to 1000 psig.

13. The process of claim 12 wherein the operating temperature is in the range from about 0° C. to about 150° C.

14. The process of claim 12 wherein the pressure is in the range from about 50 psig to about 300 psig.

15. A process for the disproportionation of 1-butene to ethylene and hexene comprising contacting 1O-butene with a catalyst containing $Re_2O_7$ or $NH_4ReO_4$ in a distillation column reactor, wherein the pressure in the reactor is in the range from about 80 psig to about 90 psig and the temperature in the overhead condenser is −50° C.

16. A process for the disproportionation of 1-butene to ethylene, propylene, pentene, and hexene comprising containing 1-butene with a catalyst containing $Re_2O_7$ in a distillation column reactor, wherein the reactor pressure is 100 psig and the temperature in the overhead condenser is about 28° C.; and wherein the catalyst has been calcined in a stream of water-saturated air.

17. A process for the disproportionation of 1-butene to propylene and pentene comprising contacting 1-butene with a catalyst containing $NH_4ReO_4$ in a distillation column reactor, wherein the reactor pressure is 90 psig and the temperature in the overhead condenser is 0° C.; and wherein the catalyst is calcined in air.

18. A process for the disproportionation of 1-butene and 2-butene to propylene and pentene comprising contacting a mixture of 1-butene and 2-butene with a catalyst containing $Re_{O7}$ in a distillation column reactor, wherein the reactor pressure is 100 psig and the temperature in the overhead condenser is about 5° C.

19. The process of claim 1 wherein the combined yield of disproportionation products is at least about 75 percent.

20. The process of claim 19 wherein the combined yield of disproportionation products is at least about 85 percent.

* * * * *

UNITED STATES PATENT AND TRADEMARK OFFICE
CERTIFICATE OF CORRECTION

PATENT NO. : 4,709,115
DATED : November 24, 1987
INVENTOR(S) : Chu W. Jung, Philip E. Garrou and Gary R. Strickler It is certified that error appears in the above-identified patent and that said Letters Patent is hereby corrected as shown below:

Column 2, line 38, after the word feedstock a new paragraph should start with U.S. Pat. No. 3,642,931 (1972). Column 5, line 21 "isnot" should read -- is not --; lines 35 - 37 "Typical yields of the process of the present invention are at least about 65 percent, based upon moles of alkene in at least about 75 percent." should read -- Typical yields of the process of the present invention are at least about 65 percent, based upon moles of alkene in the feed stream. Preferably, the yield will be at least about 75 percent. --; line 43 "pressure and" should read -- pressure, and --; at line 46 starting with the words "feed which goes to the" through line 56 ending with the words "advantageous in that a great degree" should be deleted because of printer error. Column 8, line 9 "calcuated" should read -- calculated --. Column 11, Claim 1, line 31 "reactor er such" should read -- reactor under such --. Column 12, Claim 9, line 4 "hexene" should read -- hexenes --; Claim 15, lines 30 and 31 "10-butene" should read -- 1-butene --; Claim 18, line 52 "$Re_{O7}$" should read -- $Re_2O_7$ --.

Signed and Sealed this

First Day of November, 1988

Attest:

DONALD J. QUIGG

Attesting Officer

Commissioner of Patents and Trademarks